United States Patent
Bombardelli et al.

(10) Patent No.: US 7,553,502 B2
(45) Date of Patent: Jun. 30, 2009

(54) FORMULATIONS OF ALPHA-AMYLASE INHIBITORS WITH ALPHA-GLUCOSIDASE INHIBITORS USEFUL IN THE TREATMENT OF DIABETES AND OBESITY

(75) Inventors: Ezio Bombardelli, Groppello Cairoli (IT); Paolo Morazzoni, Milan (IT); Cesare Ponzone, Milan (IT); Massimo Ronchi, Milan (IT)

(73) Assignee: Indena S.p.A., Milan (IT)

( * ) Notice: Subject to any disclaimer, the term of this patent is extended or adjusted under 35 U.S.C. 154(b) by 0 days.

(21) Appl. No.: 12/042,355

(22) Filed: Mar. 5, 2008

(65) Prior Publication Data
US 2008/0220098 A1 Sep. 11, 2008

Related U.S. Application Data

(60) Provisional application No. 60/905,319, filed on Mar. 7, 2007.

(51) Int. Cl.
*A01N 65/00* (2006.01)

(52) U.S. Cl. .................................................. 424/725
(58) Field of Classification Search ................... None
See application file for complete search history.

(56) References Cited

U.S. PATENT DOCUMENTS

2006/0189512 A1* 8/2006 Ehrenkranz ................... 513/3

* cited by examiner

*Primary Examiner*—Michael V Meller
(74) *Attorney, Agent, or Firm*—Young & Thompson

(57) ABSTRACT

This invention relates to the combination of α-amylase inhibitors prepared from *Phaseolus vulgaris* with α-glucosidase inhibitors obtained from *Salacia oblonga* and other species. The α-amylase inhibitor is accompanied by a quantity of lectins that reduces the amount of glucose originating from the starches present in the diet, and considerably reduces the appetite after repeated administration. The combination with α-glucosidase inhibitors, such as extracts of *Salacia* or the thiosugars present in it, further reduce the blood glucose, acting synergically, and consequently reduce the synthesis of fats from carbohydrates.

4 Claims, No Drawings

FORMULATIONS OF ALPHA-AMYLASE INHIBITORS WITH ALPHA-GLUCOSIDASE INHIBITORS USEFUL IN THE TREATMENT OF DIABETES AND OBESITY

FIELD OF INVENTION

The present invention relates to formulations consisting of (i) *Phaseolus vulgaris* extracts containing pharmacologically active quantities of α-amylase inhibitors and (ii) *Salacia oblonga* or *Salacia reticulata* extracts containing pharmacologically active quantities of α-glucosidase inhibitors.

BACKGROUND TO THE INVENTION

Obesity is currently one of the major health problems, especially in the industrialised countries, with serious consequences in cardiocirculatory and skeletal terms.

Carbohydrates are an important source of calories, and contribute to the synthesis of fats in individuals predisposed to obesity or type II diabetes. As hyperglycaemia leads to an increase in energy deposits, the availability of substances that reduce bioavailable glucose is very important. As starches are the main source of glucose, specific α-glucosidase and α-amylase inhibitors, obtained from plant materials or by synthesis, have been studied. It has long been known that some seeds and pulses contain substances which can have adverse effects on the diet if eaten before they are completely cooked. Many pulses contain protease inhibitors, amylase inhibitors and substances that discourage predators from continuing to use them by reducing the appetite. These substances, called phytohaemagglutinins, can cause hyperplasia of the pancreas at high doses, but can be useful in appetite control at lower doses.

At high doses, these lectins survive the intestinal transit and bond to the enterocytes where they cause the secretion of cholecystokinin, a trophic hormone that stimulates secretion by the pancreas, consequently causing its enlargement. Cholecystokinin also has favourable effects, because it reduces the appetite by reducing gastric motility.

As excess blood glucose leads to an increase in energy deposits, substances that reduce the availability of free glucose after an intake of starchy carbohydrates in the diet are very important. Most glucose originates from the breakdown of starch, which begins in the mouth due to the effect of ptyalin; this enzyme detaches saccharide chains, which in turn are converted to glucose by saccharases and α-glucosidases. α-amylase, secreted by the pancreas in the duodenum, demolishes the starch in glucose chains in the intestine, where it is converted to glucose due to the effect of α-glucosidase.

It is therefore obvious that in order to achieve a substantial reduction in the release of glucose, it is important to have both α-amylase inhibitors and α-glucosidase inhibitors.

The α-amylase inhibitor in itself considerably reduces the quantity of glucose originating from the starches present in the diet, and reduces the appetite after repeated administration.

It has now surprisingly been found that by combining *Phaseolus vulgaris* extracts with *Salacia oblonga* extracts in the ratio of between 1:1 and 1:4, a marked reduction in blood glucose is obtained in humans. It is also known that a reduced food intake leads in any event to a reduction in the accumulation of fatty deposits.

DESCRIPTION OF THE INVENTION

It has surprisingly been found that by preparing products enriched with α-amylase inhibitors having a lectin content that ensures excellent tolerability, a reduction in body weight proportional to the dose administered can be obtained. The data in rats suggested that the effect on body weight reduction was not simply associated with a reduction in the plasma glucose level, but also with a definite reduction in food consumption. Various pharmacological experiments demonstrated that this reduced food intake, despite unrestricted access to food, was associated not with a simply toxic effect, but with a modification in the desire to eat. The *Phaseolus vulgaris* extract described in PCT/EP2006/012012 is preferably used. Said extract is obtainable by extraction from *Phaseolus* sp. with mixtures of ethanol and water, and is characterised by an alpha-amylase inhibitor content of between 1200 and 1600 USP/mg (HPLC titre between 7 and 14% w/w) and a phytohaemagglutinin content of between 12,000 and 30,000 HAU/g. Said extract can be obtained by a process which comprises:

a) extraction from *Phaseolus* sp. with aqueous buffers having a pH varying between 3 and 6.5 and subsequent separation of the extract from the biomass, which can possibly be further extracted with the buffer until exhaustion in alpha-amylase and phytohaemagglutinin inhibitors;

b) filtration or centrifugation of the combined extracts and concentration to a volume corresponding to approx. 10% of the weight of the biomass of the initial extract after centrifugation;

c) differential precipitation of the concentrated aqueous extract with diluted ethanol, to a final concentration of between 60 and 70% v/v;

d) separation of the precipitate and reprecipitation from demineralised water with 60% ethanol, or diafiltration on a membrane with a 10,000 Da cut-off and drying of the precipitation residue.

The combination of an extract with α-amylase inhibitors and an extract containing α-glucosidase inhibitors, such as extracts of *Salacia oblonga* or *Salacia reticulata* root or similar commercially obtainable species, has surprisingly demonstrated an unforeseen synergic effect, with a reduction in plasma glucose levels not obtainable with the individual ingredients.

The results for the hypoglycaemic activity of the combination and the individual extracts are set out in the Table below according to the method described by Tormo MA et al., Br. J. Nutr. 96, 539, 2006.

TABLE

Effect of *Phaseolus vulgaris* extract, *Salacia oblonga* extract and their combination on glycemia in Wistar rats given a restricted amount of food with a 1 hour/day limited access

| *Phaseolus vulgaris* extract mg/kg p.o. | *Salacia oblonga* extract mg/kg p.o. | AUC of glucose plasma levels (mg/dL) |
| --- | --- | --- |
| 0 | 0 | 6850 ± 600 |
| 100 | 0 | 5500 ± 700 * (−20%) |
| 0 | 200 | 5600 ± 650 * (−18%) |
| 50 | 100 | 4500 ± 900 ** (−35%) |

Number of animal/group: 8
* $p < 0.05$
** $p < 0.01$ vs controls

The administration of the individual compounds and the corresponding combination did not have any toxic effect at doses of up to 2000 mg/kg for three months.

The present invention allows the preparation of products useful in the treatment of obesity, excess weight and type II diabetes, and in diets designed to maintain a constant body weight.

In order to be effective on blood glucose and to be effective on weight control in long-term treatments, the two extracts are combined in a ratio of between 1:1 and 1:4; the doses range from 50 to 200 mg for the *Phaseolus vulgaris* extract and from 200 to 600 mg for the *Salacia* extract, depending on the active constituent content measured by HPLC. The formulations according to the invention can take the form of soft or hard gelatin capsules, cellulose capsules, tablets or liquid forms, and the extracts can be separately formulated in totally or partly gastroresistant forms. The products should be taken at main meals or whenever foods rich in carbohydrates are eaten. The formulation can also be associated with substances that reduce gas formation in the colon or partly absorb the excess.

The following examples illustrate the invention in detail.

EXAMPLE 1

Formulation of *Phaseolus vulgaris* and *Salacia oblonga* Extracts into Hard Gelatin Capsules Unit Composition:

| | |
|---|---|
| *Phaseolus vulgaris* dried extract | 50 mg |
| *Salacia oblonga* dried extract | 200 mg |
| Microcrystalline cellulose | 120 mg |
| Mannitol | 100 mg |
| Simeticone | 20 mg |
| Silicon dioxide | 10 mg |

Manufacturing Process:

Adsorb the simeticone on the mannitol and on part of the microcrystalline cellulose.

Mix the resulting product with *Phaseolus vulgaris* dried extract, *Salacia oblonga* dried extract, the remainder of the microcrystalline cellulose and the silicon dioxide.

Divide the mixture between hard gelatin capsules.

EXAMPLE 2

Formulation of *Phaseolus vulgaris* and *Salacia oblonga* Extracts into Tablets

Unit Composition:

| | |
|---|---|
| *Phaseolus vulgaris* dried extract | 100 mg |
| *Salacia oblonga* dried extract | 150 mg |
| Microcrystalline cellulose | 150 mg |
| Mannitol | 100 mg |
| Cross-linked sodium carboxymethylcellulose | 30 mg |
| Silicon dioxide | 8 mg |
| Magnesium stearate | 5 mg |

Manufacturing Process:

Mix the *Phaseolus vulgaris* dried extract, *Salacia oblonga* dried extract, microcrystalline cellulose, mannitol, crosslinked sodium carboxymethylcellulose and silicon dioxide for 10 minutes.

Add the magnesium stearate to the mixture and proceed with mixing for a further 2 minutes.

Compress the mixture obtained in the preceding point.

EXAMPLE 3

Formulation of *Phaseolus vulgaris* and *Salacia oblonga* Extracts into Modified-Release Granules Unit Composition:

| | |
|---|---|
| *Phaseolus vulgaris* extract | 50 mg |
| *Salacia oblonga* extract | 100 mg |
| Microcrystalline cellulose | 100 mg |
| Povidone | 10 mg |
| Sodium carboxymethylcellulose | 8 mg |
| Methacrylic acid copolymer | 50 mg |
| Triethyl citrate | 3.2 mg |
| Talc | 8 mg |
| Simeticone | 0.3 mg |

Manufacturing Process:

Granulate the extracts, microcrystalline cellulose and sodium carboxymethylcellulose with an aqueous solution of povidone.

Dry and calibrate the granulate obtained.

Coat the granules with an aqueous suspension of methacrylic acid copolymer, triethyl citrate, talc and simeticone.

EXAMPLE 4

Formulation of *Phaseolus vulgaris* and *Salacia oblonga* Extracts into Immediate-Release Granules Unit Composition:

| | |
|---|---|
| *Phaseolus vulgaris* extract | 50 mg |
| *Salacia oblonga* extract | 100 mg |
| Microcrystalline cellulose | 100 mg |
| Povidone | 10 mg |
| Sodium carboxymethylcellulose | 8 mg |

Manufacturing Process:

Granulate the extracts, microcrystalline cellulose and sodium carboxymethylcellulose with an aqueous solution of povidone.

Dry and calibrate the granulate obtained.

EXAMPLE 5

Mixture of Granulates of *Phaseolus vulgaris* and *Salacia oblonga* Extracts with Different Release Profiles Manufacturing Process:

Mix 50% of the granulate described in example 3 with 50% of the granulate described in example 4.

Divide the mixture obtained between hard gelatin capsules.

The invention claimed is:

1. A formulation consisting of (i) *Phaseolus vulgaris* extracts containing pharmacologically active quantities of α-amylase inhibitors and (ii) *Salacia oblonga* or *Salacia*

*reticulata* extracts containing pharmacologically active quantities of α-glucosidase inhibitors.

2. The formulation as claimed in claim 1, wherein the *Phaseolus vulgaris* extract is characterised by an alpha-amylase inhibitor content of between 1200 and 1600 USP/mg (HPLC titre between 7 and 14% w/w) and a phytohaemagglutinin content of between 12,000 and 30,000 HAU/g.

3. The formulation as claimed in claim 1, wherein the *Phaseolus vulgaris* and *Salacia oblonga* or *Salacia reticulata* extracts have a weight ratio of between 1:1 and 1:4.

4. The formulation as claimed in claim 2, wherein the *Phaseolus vulgaris* and *Salacia oblonga* or *Salacia reticulata* extracts have a weight ratio of between 1:1 and 1:4.

* * * * *